(12) United States Patent
Self

(10) Patent No.: US 7,905,891 B2
(45) Date of Patent: Mar. 15, 2011

(54) SUCTION CLIP

(75) Inventor: Thomas Gregory Self, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 898 days.

(21) Appl. No.: 11/769,262

(22) Filed: Jun. 27, 2007

(65) Prior Publication Data

US 2008/0009886 A1 Jan. 10, 2008

Related U.S. Application Data

(60) Provisional application No. 60/818,603, filed on Jul. 5, 2006.

(51) Int. Cl.
*A61B 17/10* (2006.01)
(52) U.S. Cl. .................................................. 606/142
(58) Field of Classification Search .................. 606/142, 606/139, 151, 157, 213; 604/540; 600/564
See application file for complete search history.

(56) References Cited

U.S. PATENT DOCUMENTS

| 1,805,471 | A | | 5/1931 | England |
|---|---|---|---|---|
| 2,385,207 | A | * | 9/1945 | Hunn .............................. 606/201 |
| 3,759,289 | A | * | 9/1973 | DeWall .......................... 137/844 |
| 4,857,061 | A | * | 8/1989 | Miller ........................... 604/207 |
| 5,766,189 | A | | 6/1998 | Matsuno |
| 5,902,310 | A | * | 5/1999 | Foerster et al. ............... 606/142 |
| 5,908,379 | A | | 6/1999 | Schaefer et al. |
| 2004/0044364 | A1 | | 3/2004 | DeVries et al. |
| 2004/0138645 | A1 | * | 7/2004 | Lonky ............................ 604/540 |
| 2005/0070825 | A1 | * | 3/2005 | Hagiwara ........................ 601/6 |

FOREIGN PATENT DOCUMENTS

| CH | 147 282 A | 5/1931 |
|---|---|---|
| EP | 1 473 014 A1 | 11/2004 |
| EP | 1 561 420 A2 | 8/2005 |
| GB | 2 118 238 A | 10/1983 |
| WO | WO 2006/041014 A1 | 4/2006 |

* cited by examiner

*Primary Examiner* — (Jackie) Tan-Uyen T Ho
*Assistant Examiner* — Christina Lauer
(74) *Attorney, Agent, or Firm* — Brinks Hofer Gilson & Lione

(57) ABSTRACT

A suction clip and system and method therefor. The suction clip is configured for deployment from a catheter to provide for hemostasis of injured tissue. The suction clip preferably includes a flexible distal rim configured to form sealing contact with tissue to be treated and a proximal check valve to maintain a seal of the clip to the tissue when a vacuum has been provided therebetween. The suction clip may include a visual or radio-opaque marker to aid in later location of same.

12 Claims, 5 Drawing Sheets

SUCTION CLIP

CROSS-REFERENCE TO RELATED APPLICATIONS

This application claims priority to U.S. Provisional Application Ser. No. 60/818,603, filed Jul. 5, 2006, which is incorporated herein by reference in its entirety.

FIELD OF THE INVENTION

The present invention relates to a medical device for use in endoscopic surgery, and more particularly relates to a suction-clip device configured to deploy clips appropriate for hemostasis or location-marking.

BACKGROUND

Gastrointestinal bleeding is a somewhat common and serious condition that may be fatal if left untreated. This problem has prompted the development of a number of endoscopic therapeutic approaches to achieve hemostasis such as the injection of sclerosing agents and contact thermo-coagulation techniques. Although such approaches are often effective, bleeding may continue for many patients and corrective open surgery therefore becomes necessary. Because open surgery is an invasive technique that is associated with a higher morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples, sutures, and other similar devices that are able to apply sufficient constrictive forces to blood vessels so as to limit or interrupt blood flow. One of the problems associated with many conventional hemostatic devices, however, is that they can only be delivered using rigid shafted instruments via incision or trocar cannula.

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

One proposed solution is described in U.S. Pat. No. 5,766,189, which shows a clip device having a pair of arms that are provided with a tendency to open. One problem with this clip and other similar types of clips having a pair of arms is that it may often be necessary to rotate the clip to properly grasp the area to be clipped. Rotation of the clip is often hindered or complicated by the travel of the operating wire through the bends of the tube(s) used to deliver the clip. Accordingly, there is a need for a clip that can be delivered to the target area and used without having to rotate the clip to a desired orientation.

Another problem often encountered with conventional hemostatic devices is the difficulty in securing the clip device to the delivery apparatus prior to reaching the target area within the patient, and then quickly and easily releasing the clip device from the delivery apparatus once the clip has been attached to the target site.

BRIEF SUMMARY

Embodiments of the present invention may include a suction clip device that may be introduced via a minimally invasive surgical technique (such as, for example, an endoscope deployed through the alimentary canal) and that does not need to be rotated to a specific orientation to engage tissue in need of hemostatic treatment.

In one aspect, the present invention includes a suction clip device configured for marking or hemostatic treatment of tissue. The suction clip device has an enlarged distal suction chamber portion including a distal lip configured to conform to a body tissue surface, an intermediate portion comprising a check valve, and a proximal portion configured for contact with a vacuum source.

In another aspect, the invention includes a suction clip system configured for marking or hemostatic treatment of tissue. The suction clip system includes an elongate delivery catheter having a delivery lumen disposed between a proximal delivery catheter end and a distal delivery catheter end. The distal delivery catheter delivery end has an enlarged lumen portion that defines an enlarged lumenal space. The system also includes an elongate suction catheter slidably disposed through at least a portion of the delivery lumen, and the suction catheter has a suction lumen disposed between a proximal suction catheter end and a distal suction catheter end. The system also includes a suction clip member at least partially removably disposed in the delivery lumen. The suction clip member has distal suction chamber portion including a distal lip configured to conform to a body tissue surface, and the distal suction chamber portion is disposed in the enlarged lumenal space of the delivery catheter. The suction clip member also has an intermediate portion including a check valve and a proximal portion configured for connection with a vacuum source. The distal suction chamber portion is configured to be in fluid communication with the suction lumen when the check valve is in an open state.

In yet another aspect, the invention includes a method of promoting hemostasis. The method includes the steps of providing a tissue surface; providing a suction clip system as just described; positioning the distal delivery catheter delivery end such that at least a part of the flared lumen portion is immediately adjacent the tissue surface and such that the distal lip of the suction chamber portion contacts the tissue surface; providing a proximally directed suction force sufficient to create a vacuum within the distal suction chamber portion; and actuating the check valve to a closed state such that the suction clip member is suctionally adhered to the tissue.

DETAILED DESCRIPTION

Generally, a suction clip of the present invention preferably is configured to be sealed to a tissue surface in need of hemostasis. In a preferred method of use a suction clip of the present invention is suctionally adhered to a tissue surface in need of hemostasis and remains attached thereto as a mechanical hemostasis means for a time sufficient to allow the tissue to achieve hemostasis by activation of the coagulation cascade. In one application, the suction clip may affect complete mechanical hemostasis, allowing tissue adjacent the clip to heal, and tissue trapped within the clip to necrotize until the trapped tissue and clip are naturally released from the adjacent tissue in a manner similar to the banding technique known in the art and used, for example, for polyp and hemorrhoid removal. The suction clip and method of use may also be employed for marking tissue.

Figure 1:
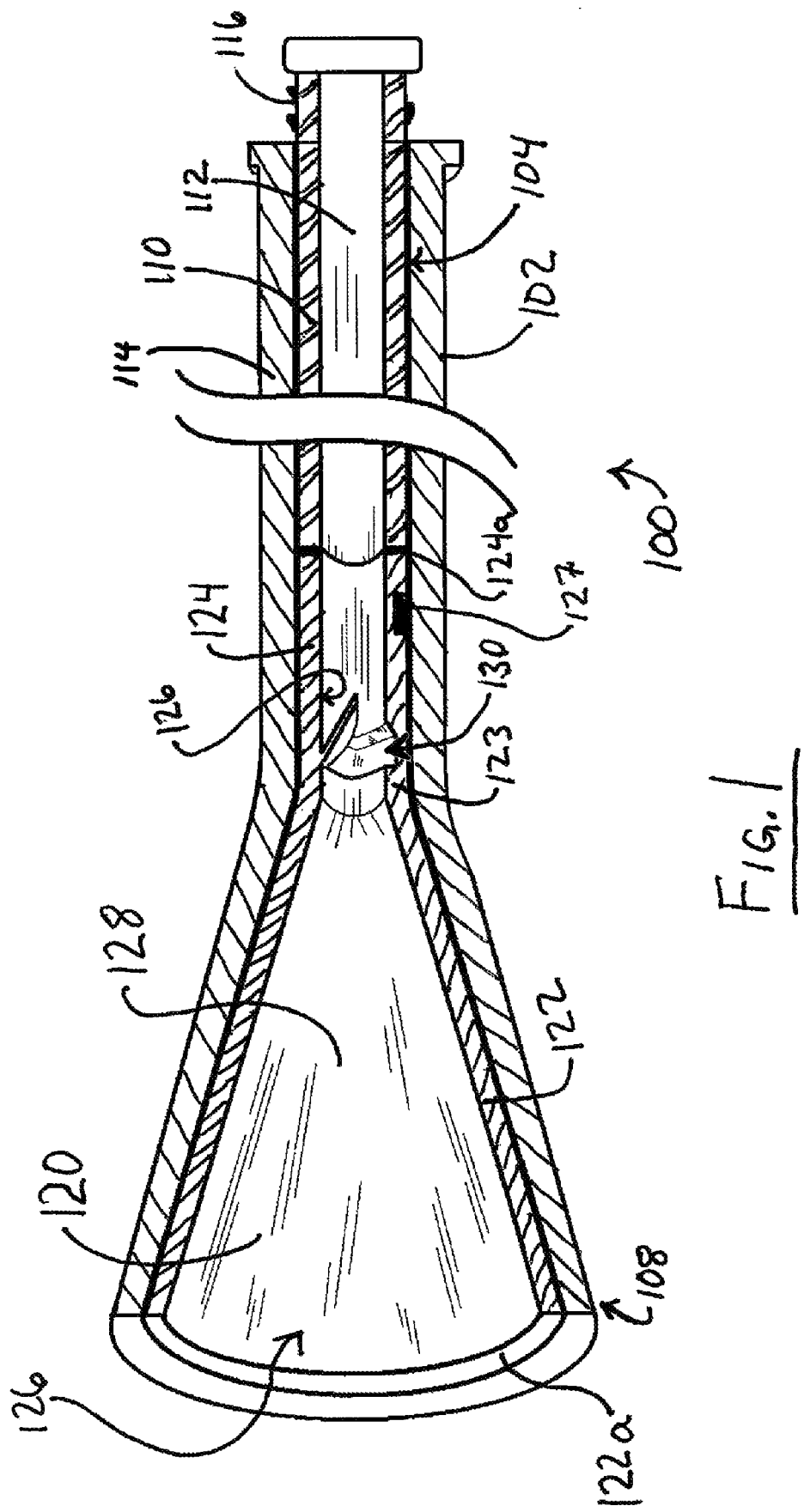
FIG. 1 is a perspective view of a longitudinally sectioned suction clip system of the present invention.
Figure 1A:
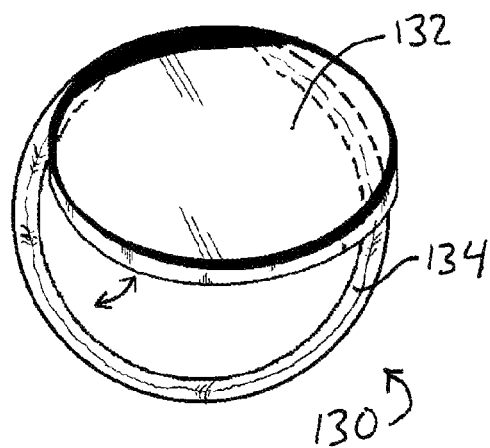
FIG. 1A shows an end-view of the check valve embodiment of FIG. 1A, in an open state.
Figure 1B:
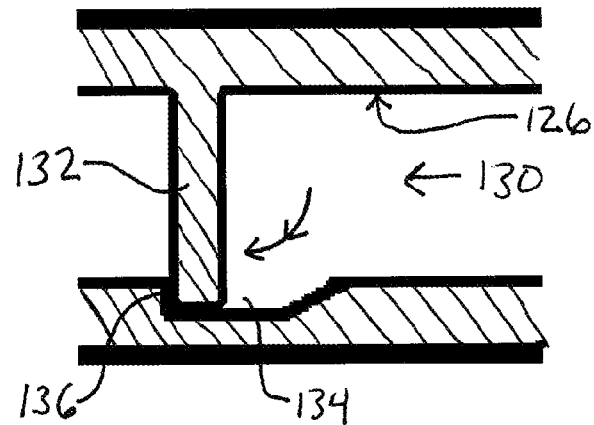
FIG. 1B depicts a cross-sectional view of a check valve embodiment of the present invention in a closed state.
Figure 1C:
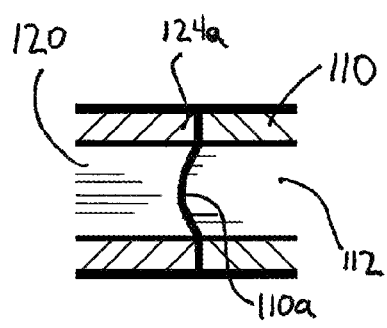
FIG. 1C illustrates a first embodiment of a suction clip-suction catheter connection.
Figure 1D:
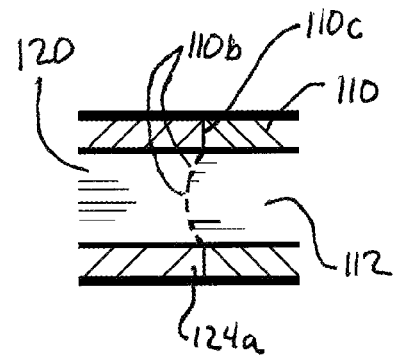
FIG. 1D shows a second embodiment of a suction clip-suction catheter connection.

In one aspect, illustrated in the perspective, longitudinal cross-sectional views of FIGS. 1-1D, the present invention includes a suction clip delivery system 100. The suction clip delivery system 100, shown in FIG. 1, includes an elongate delivery catheter 102 having a delivery lumen 104 disposed through at least a portion of its length. The distal end portion 108 of the delivery catheter 102 preferably is enlarged (relative to a proximal portion of the catheter). In the illustrated embodiment, the distal end portion 108 is generally frustoconical and houses a suction clip 120 that is configured to be deployed therefrom. In a preferred embodiment, the largest outer diameter of the distal end of the delivery catheter 102 is about 4 mm, which permits the suction clip system 100 to be used with a 4.2 mm channel endoscope. The delivery catheter 102 preferably is constructed of a material having sufficient column strength to transfer pushing force from its proximal end to its distal end while not radially collapsing when a vacuum is generated through the delivery lumen 104. At the same time, the delivery catheter 102 preferably retains sufficient flexibility to be manipulated through an endoscope. One exemplary material for construction of the delivery catheter 102 is PEEK tubing.

A suction catheter 110 preferably is disposed through at least a portion of the delivery lumen 104. In an initial deployment state, a distal end 114 of the suction catheter 110 preferably contacts a proximal end rim 124a of the suction clip 120. The suction catheter 110 includes a suction lumen 112. The proximal end of the suction catheter 110 preferably includes a Luer fitting 116 to engage a syringe (not shown) or other means for exerting a vacuum through the suction lumen 112. The suction catheter 110 preferably includes a lubricious outer surface that allows it to be moved axially within the delivery lumen 104, while not allowing a vacuum generated through the suction lumen 112 to be lost through the interface between the suction catheter 110 and the delivery lumen 104.

The suction clip 120 is generally funnel-shaped, including a distal portion 122 that is generally frustoconical and a proximal portion 124 that is generally tubular. It should be appreciated that other, non-frustoconical geometries of the suction clip 120 and the distal suction catheter end 114 may provide an enlarged area and volume suitable for use with the present invention (e.g., bell-shaped, pyriform). An intermediate transition portion 123 between the distal and proximal portions 122, 124 preferably has a smooth, curved contour rather than being sharply angled. The transition portion 123 houses a check valve 130. The clip is preferably constructed of PTFE, silicone, or some other synthetic plastic or elastomer. The distal portion preferably is sufficiently flexible to conform to a tissue surface well enough to maintain a vacuum seal. Specifically, in a preferred embodiment, the material of the distal portion 122, and particularly a distal rim 122a of the distal portion 122, is sufficiently radially flexible to conform to a tissue surface, and is sufficiently longitudinally rigid to maintain a suctional seal between the tissue surface and the check valve 130 without collapsing on itself. In a preferred embodiment the proximal portion 124 preferably is thicker than the distal portion to provide adequate rigidity before and during deployment. Alternatively, the proximal portion 124 may be constructed from a different material. The interior clip surface 126 defines a suction chamber 128. The proximal end rim 124a of the suction clip 120 preferably includes a retention means to help retain the suction clip in the delivery catheter 102 until deployment by a user. The retention means illustrated includes a resilient proximal end rim 124a, which is biased into an outer diameter that is greater than the inner diameter of the delivery catheter's delivery lumen 104, such that the suction clip 120 is frictionally retained therein until being displaced by user-directed distal movement of the suction catheter 110.

In other embodiments, the proximal end rim 124a of the suction clip 120 may be removably attached to the suction catheter 110. Two such embodiments are shown in FIGS. 1C-1D, which are detail illustrations of the attachment between the suction clip 120 and the suction catheter 110. In FIG. 1C, an impermanent adhesive seam 110a connects the proximal suction clip rim 124a to the suction catheter 110. In FIG. 1D, the surface of the suction clip 120 is generally continuous with the surface of the suction catheter 110, but has perforations 110b along a seam 110c where the proximal suction clip rim 124a meets the distal end of the suction clip 110. With either or both of these retention/release means, the delivery catheter 102 can be used to hold the suction clip 120 in place while the suction catheter 110 is retracted proximally and separated therefrom. In other embodiments, not shown, the distal portion of the suction clip or of the delivery catheter may include a stiffening means such as longitudinal, radial, and/or helical wire(s) disposed in or on the wall of one or both of those structures. Such wire(s) may be constructed of nitinol, stainless steel, or a polymer, preferably with at lease slightly greater rigidity than the adjacent wall.

One embodiment of a check valve 130 is described with reference to FIGS. 1A-1B, which are magnified detail images from FIG. 1. Specifically, FIG. 1A shows an end-view of the check valve 130, and FIG. 1B provides a cross-sectional view of the check valve 130 in a closed state. The check valve 130 includes a valve flap 132 and a valve seat groove 134. The valve flap 132 is generally circular and preferably is formed continuously with the interior clip surface 126. Preferably, the valve flap 132 is biased at a slightly proximal angle to allow a vacuum to be generated within the interior clip surface 126 before the vacuum pulls shut the valve flap. The valve seat groove 134 preferably is also formed continuously with the interior clip surface 126 and is configured to provide an airtight seal 136 when in contact with the distal surface of the valve flap 132.

A method of use is described with reference to FIGS. 2A-2D. A preferred method of use of the system 100 is for hemostatic treatment of an injured tissue region 160 having a diameter of less than about 4 mm.

Figure 2A:
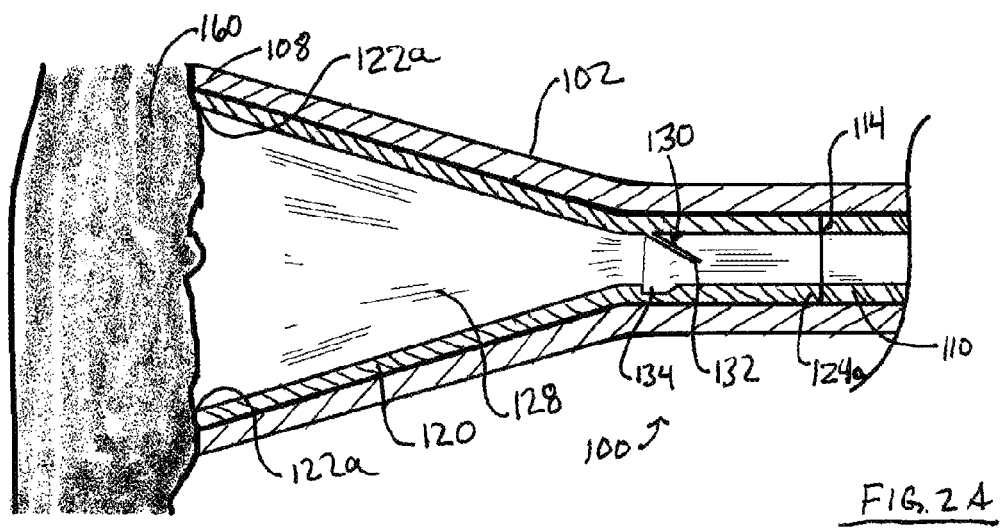
FIGS. 2A-2D depict a method of the present invention.

FIG. 2A depicts a longitudinal cross-sectional view of the suction clip system 100, having been positioned in contact with injured tissue 160 (It should be appreciated that the tissue 160 need not be injured, for example, if the suction clip is being applied as a marker). As shown in FIG. 2A, the check valve 130 is biased in an open position, the distal end 108 of the delivery catheter 102 contacts tissue adjacent the injured tissue 160, and the distal rim 122a of the suction clip 120 is placed in sealing contact about the injured tissue 160. The distal end 114 of the suction catheter 110 is in contact with the proximal end of the suction clip 120. In preferred embodiment this contact is not necessary to build or maintain a vacuum sufficient for actuation and deployment of the suction clip 120.

Figure 2B:
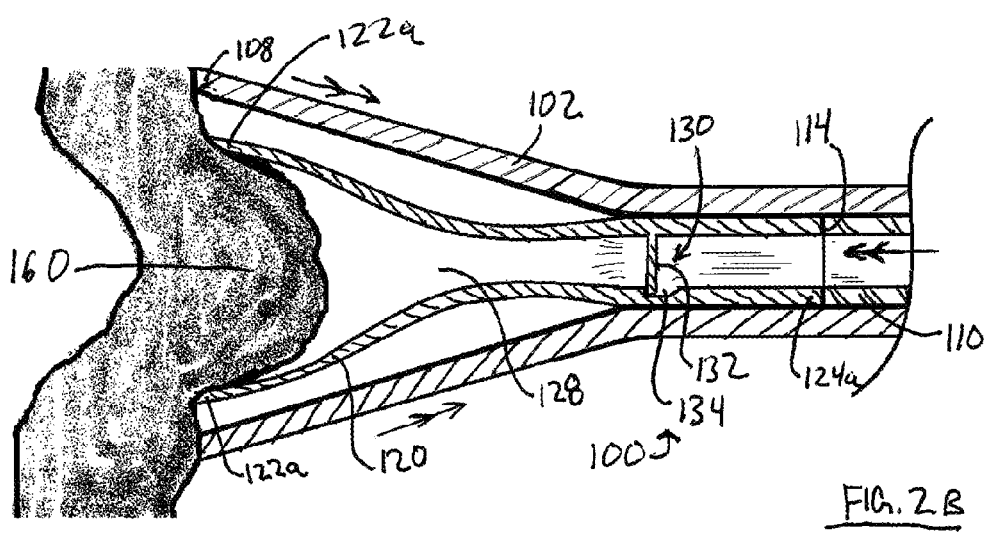

As shown in FIG. 2B, a vacuum has been generated in the suction chamber 128 through the suction catheter 110 (e.g., by suction having been exerted through a syringe or other suction source, not shown). The vacuum is sufficient to draw at least a portion of the injured tissue 160 into the suction chamber 128 of the suction clip 120, and to begin collapsing the distal suction clip portion 122 around the injured tissue 160. It is most preferable that the suction clip distal rim 122a maintain sealing contact with the injured tissue 160 or adjacent tissue. As is also shown in FIG. 2B, the vacuum in the suction chamber 128 is sufficiently strong to overcome the proximal bias of the check valve flap 132, thereby drawing it into sealing contact with the valve seat 134. Most preferably, the distal seal of the suction clip rim 122a with the injured tissue 160 and the proximal seal of the check valve 130 are sufficient to provide hemostasis of the injured tissue 160 and to retain the suction clip 120 on the tissue upon removal of the delivery catheter 102 and the suction catheter 110.

Figure 2C:
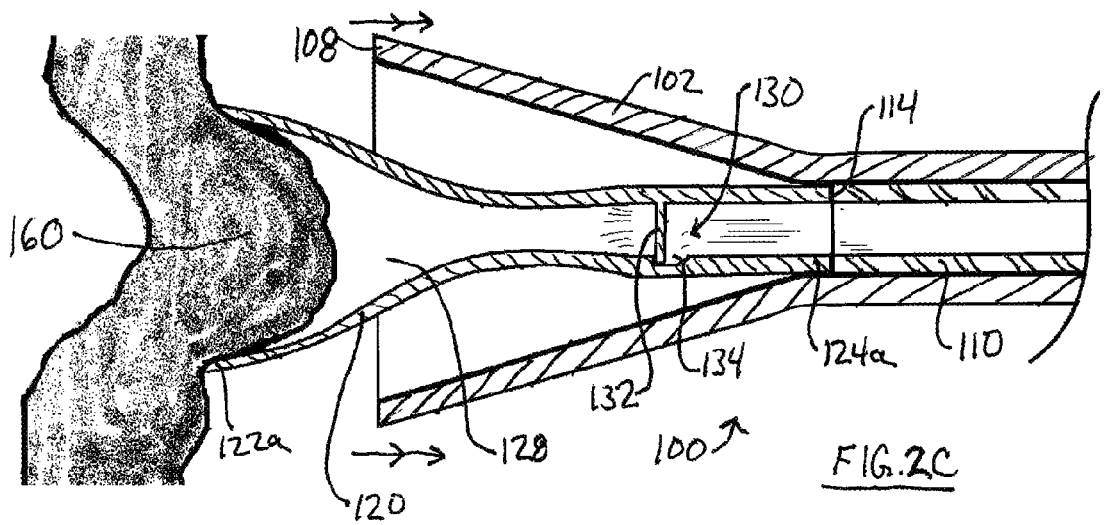

Next, as shown in FIG. 2C, the delivery catheter 102 may be withdrawn proximally, while advancing or at least leaving the suction catheter 110 in contact with the proximal rim 124a of the suction clip 120. In the illustrated embodiment, the retraction of the delivery catheter 102 releases the frictional retention of the proximal suction clip rim 124a with the inner surface of the delivery lumen 104. If other release/retention means are used, both the delivery and suction catheters 102, 110 may be withdrawn at the same time, or the suction catheter 110 may be withdrawn first, in accordance with the particular actuation requirements associated with those release/retention means.

Figure 2D:
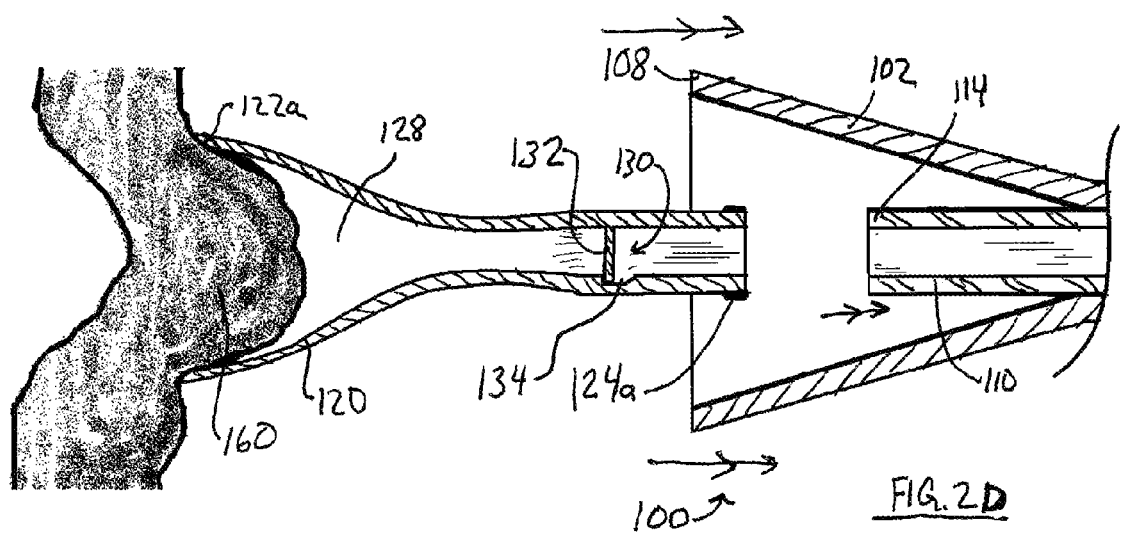

Finally, as shown in FIG. 2D, the suction catheter 110 is retracted, and the suction clip 120 is left suctionally attached to the injured tissue 160. In alternative embodiments of the method, a suction clip may be deployed onto tissue that is not injured. For example a suction clip may be provided, with a brightly colored exterior or with one or more radio-opaque markings to be used for visualization. As one example, a suction clip including a marking 127 may be placed adjacent a duodenal site to be treated in order to provide for ease of later navigation of an endoscopic tool to that site. In this example, the marking may be radio-opaque (e.g., for use in later fluoroscopic navigation or location of a particular site) or may include a visible marking such as a bright color, a fluorescent/luminescent marking, or even an LED or other light source, or any combination thereof (e.g., for use in later visual navigation).

Figure 3A:
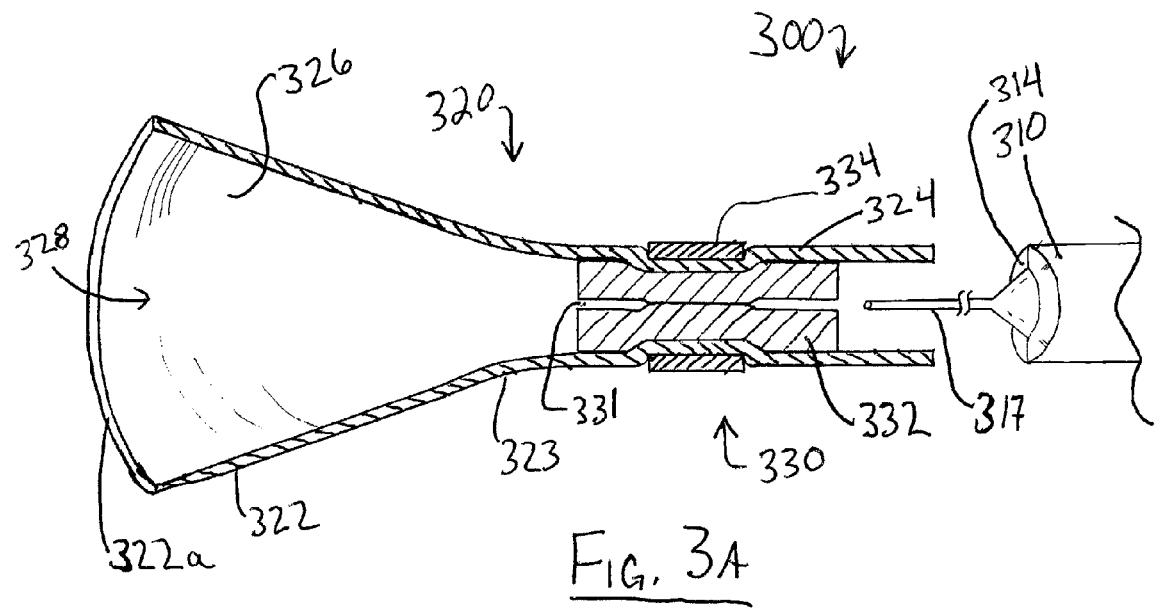
FIGS. 3A-3B illustrate generally tubular check valve embodiments.

In another aspect, illustrated in the longitudinal cross-sectional view of FIG. 3A, the present invention includes a suction clip delivery system 300. The suction clip delivery system 300, shown in FIG. 3A, includes an elongate delivery catheter (not shown) having a delivery lumen disposed through at least a portion of its length. The delivery catheter preferably is constructed of a material having sufficient column strength to transfer pushing force from its proximal end to its distal end while not radially collapsing when a vacuum is generated through the delivery lumen. At the same time, the delivery catheter preferably retains sufficient flexibility to be manipulated through an endoscope.

A suction catheter 310 preferably is disposed through at least a portion of the delivery lumen. In an initial deployment state, a distal end 314 of the suction catheter 310 preferably contacts a proximal end rim of the suction clip 320. The suction catheter 310 includes a suction lumen 312. A generally tubular needle 317 projects distally from the suction catheter 310 and includes a needle lumen that preferably is continuous with the suction lumen 312. The suction catheter 310 preferably includes a lubricious surface that allows it to be moved axially within the delivery lumen, while not allowing a vacuum generated through the suction lumen 312 to be lost through the interface between the suction catheter 310 and the delivery lumen.

The suction clip 320 is generally funnel-shaped, including a distal portion 322 that is generally frustoconical and a proximal portion 324 that is generally tubular. It should be appreciated that other, non-frustoconical geometries of the suction clip 320 and the distal suction catheter end may provide an enlarged area and volume suitable for use with the present invention (e.g., bell-shaped, pyriform). An intermediate transition portion 323 between the distal and proximal portions 322, 324 preferably has a smooth, curved contour rather than being sharply angled. The transition portion 323 houses a check valve 330. The distal portion 322 preferably is sufficiently flexible to conform to a tissue surface well enough to maintain a vacuum seal. Specifically, in a preferred embodiment, the material of the distal portion 322, and particularly a distal rim 322a of the distal portion 322, is sufficiently radially flexible to conform to a tissue surface, and is sufficiently longitudinally rigid to maintain a suctional seal between the tissue surface and the check valve 330 without collapsing on itself. In a preferred embodiment the proximal portion 324 preferably is thicker than the distal portion to provide adequate rigidity before and during deployment. Alternatively, the proximal portion 324 may be constructed from a different material. The interior clip surface 326 defines a suction chamber 328. The proximal end rim of the suction clip 320 may include a retention means to help retain the suction clip in the delivery catheter until deployment by a user.

Another embodiment of a check valve 330 is described with reference to FIG. 3A, provides a cross-sectional view of the check valve 330 in a closed state. The check valve 330 includes a generally tubular sealing member 332 (preferably formed of silicone or a similar material) disposed in the proximal clip portion 324 and a crimping band 334 that is disposed radially around the sealing member 332 and at least a part of the proximal clip portion 324. The crimping band 334 biases the sealing member 332 into a closed position. During deployment and actuation to provide a seal between the suction clip 320 and a tissue surface, the needle 317 is directed through a central longitudinal lumen 331 of the sealing member 332 so that a vacuum may be generated therethrough in the distal clip portion 322. When the clip 320 is sealed to the tissue surface, the needle 317 may be withdrawn and the crimping member bias will close the lumen 331 of the sealing member 332 to maintain a vacuum seal between the clip 320 and the tissue.

Figure 3B:
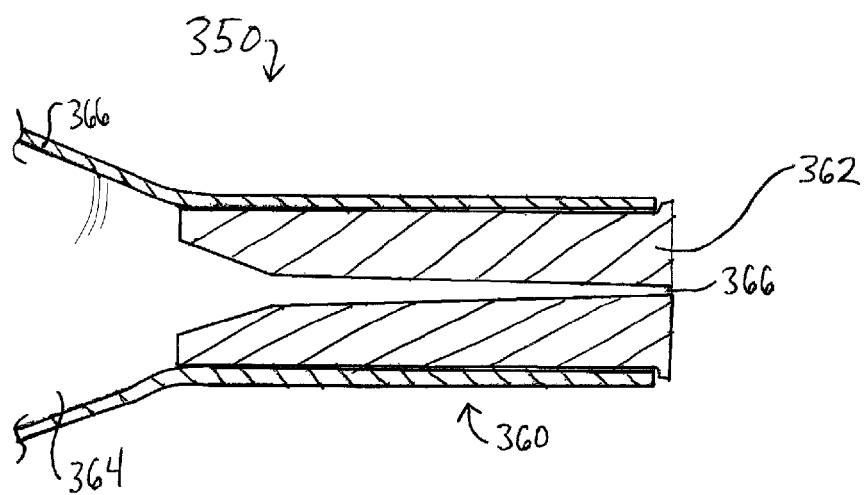

FIG. 3B shows a partial cross-section of another embodiment of a suction clip 350, including a check valve 360 and an enlarged distal vacuum chamber 364 circumferentially defined by a wall 366. The check valve 360 preferably is a generally tubular silicone sealing member 362. The sealing member 362 includes a sealing lumen 366, which extends generally along the length of a central longitudinal axis of the sealing member 362, and preferably has a proximal inner diameter smaller than its distal internal diameter. The sealing lumen 366 has a narrower proximal end portion than its distal end portion. When the suction clip 350 is placed against tissue and suction drawn therethrough as with the above embodiments, a vacuum is generated in the vacuum chamber 364. In a preferred embodiment, the material of the sealing member 362 is sufficiently flexible that, when a vacuum exists in the vacuum chamber 364, the sealing lumen 366 collapses radially shut to seal the chamber 364 and maintain the vacuum therein. The embodiment shown in FIG. 3B may be used with a needle-bearing suction catheter such as is illustrated in FIG. 3A, or may be used with a suction catheter such as is illustrated in FIGS. 1-2D. Other "collapsible" check valve devices may be used within the scope of the present invention.

Those of skill in the art will appreciate that variants of the suction clip device described herein may also be practiced within the scope of the present application. It is therefore intended that the foregoing detailed description be regarded as illustrative rather than limiting. It should be understood that the following claims, including all equivalents, are intended to define the spirit and scope of this invention.

I claim:

1. A suction clip system configured for marking or hemostatic treatment of tissue, the suction clip system comprising:
    an elongate delivery catheter having a delivery lumen disposed between a proximal delivery catheter end and a distal delivery catheter end, wherein the distal delivery catheter delivery end comprises an enlarged lumen portion defining an enlarged lumenal space;
    an elongate suction catheter slidably disposed through at least a portion of the delivery lumen, the suction catheter including a suction lumen disposed between a proximal suction catheter end and a distal suction catheter end; and
    a suction clip member at least partially removably disposed in the delivery lumen and comprising
        a distal suction chamber portion including a distal lip configured to conform to a body tissue surface, wherein the distal suction chamber portion is disposed in the enlarged lumenal space of the delivery catheter;
        an intermediate portion comprising a check valve; and
        a proximal portion configured for connection with a vacuum source; and wherein the distal suction chamber portion is in fluid communication with the suction lumen when the check valve is in an open state.

2. The suction clip system of claim 1, wherein the proximal suction catheter end comprises a structure configured for attaching a vacuum source.

3. The suction clip system of claim 1, wherein the distal suction catheter end is mechanically connected to the proximal surface of the suction clip member.

4. The suction clip system of claim 3, wherein the mechanical connection is selected from a releasable adhesive bond, a perforation, and a combination thereof.

5. The suction clip system of claim 1, wherein the check valve is biased into an open state.

6. The suction clip system of claim 1, wherein the check valve occupies one of an open state and a closed state,
    said closed state comprising a substantially gas-impermeable seal; and
    said closed state being promoted by exertion of a proximally directed vacuum through the distal suction chamber portion and a contact between the distal lip and a surface.

7. The suction clip system of claim 1, wherein the check valve comprises a flap and complementary groove configured to provide a substantially gas-impermeable seal when in a closed state.

8. The suction clip system of claim 1, wherein the check valve comprises a generally tubular member having a lumen therethrough, said lumen configured to sealingly collapse to maintain a vacuum in the enlarged distal suction chamber portion.

9. The suction clip system of claim 1, wherein the elongate suction catheter comprises a generally tubular needle portion.

10. The suction clip system of claim 1, wherein the enlarged lumen portion comprises a generally frustoconical shape.

11. A method of promoting hemostasis, the method comprising the steps of:
    providing a tissue surface;
    providing the suction clip system of claim 1;
    positioning the distal delivery catheter delivery end such that at least a part of the flared lumen portion is immediately adjacent the tissue surface and such that the distal lip of the suction chamber portion contacts the tissue surface;
    providing a proximally directed suction force sufficient to create a vacuum within the distal suction chamber portion; and
    actuating the check valve to a closed state such that the suction clip member is suctionally adhered to the tissue.

12. The method of claim 11, wherein a mechanical attachment is provided between the suction catheter and the suction clip member, and further comprising the step of separating said mechanical attachment.

* * * * *